US008066651B2

(12) United States Patent
Richard Vitton

(10) Patent No.: US 8,066,651 B2
(45) Date of Patent: Nov. 29, 2011

(54) EXAMINATION CHAIR

(76) Inventor: Thomas Richard Vitton, Ventabren (FR)

( * ) Notice: Subject to any disclaimer, the term of this patent is extended or adjusted under 35 U.S.C. 154(b) by 803 days.

(21) Appl. No.: 10/579,240

(22) PCT Filed: Nov. 12, 2004

(86) PCT No.: PCT/FR2004/002909
§ 371 (c)(1),
(2), (4) Date: Jul. 10, 2006

(87) PCT Pub. No.: WO2005/048907
PCT Pub. Date: Jun. 2, 2005

(65) Prior Publication Data
US 2007/0106184 A1    May 10, 2007

(30) Foreign Application Priority Data

Nov. 14, 2003   (FR) ..................................... 03 13367
Jul. 12, 2004   (FR) ..................................... 04 07743

(51) Int. Cl.
*A61H 1/00*     (2006.01)
*A61H 1/02*     (2006.01)
*A61H 5/00*     (2006.01)
*A63G 1/00*     (2006.01)
*A61B 1/06*     (2006.01)
*A61B 13/00*    (2006.01)
*A61B 5/117*    (2006.01)

(52) U.S. Cl. ............ 601/24; 472/47; 600/300; 600/558; 600/595; 128/897; 73/432.1

(58) Field of Classification Search .................... 434/55; 472/47; 600/595, 300, 558; 601/86, 90, 601/98–100, 24, 25; 606/244; 128/845, 128/897, 898
See application file for complete search history.

(56) References Cited

U.S. PATENT DOCUMENTS 1,342,871 A  *   6/1920   Ruggles .......................... 434/55
(Continued)

FOREIGN PATENT DOCUMENTS
FR            1 113 809         4/1956

OTHER PUBLICATIONS

Furman et al., "Treatment of Benign Positional Vertigo Using Heels-over-Head Rotation," *Annals of Otology, Rhinology and Laryngology*, 1998, vol. 107, pp. 1046-1053.

*Primary Examiner* — Max Hindenburg
*Assistant Examiner* — John Pani
(74) *Attorney, Agent, or Firm* — Brooks Kushman P.C.

(57) ABSTRACT

A medical examination chair is used to seat a patient and move the patient along three essentially-perpendicular planes over a wide range. The chair includes a primary arc which is connected to a stationary column by a horizontal shaft, forming a first axis of rotation. A second axis of rotation, which is essentially perpendicular to the first, passes through first and second ends of the primary arc. The chair also includes a secondary arc which is equipped with a seat and which is disposed inside the primary arc. Third and fourth ends of the secondary arc are connected to the first and second ends of the primary arc by an upper shaft and a lower shaft. The primary and secondary arcs can rotate around the first and second axes of rotation respectively. The medical examination chair further includes braking elements for suddenly stopping the rotational movement.

4 Claims, 3 Drawing Sheets

U.S. PATENT DOCUMENTS

| | | | | |
|---|---|---|---|---|
| 2,832,245 A * | 4/1958 | Burrows | | 81/125 |
| 3,343,875 A * | 9/1967 | Ferrara | | 297/410 |
| 3,716,046 A * | 2/1973 | Janeke | | 600/546 |
| 3,774,963 A * | 11/1973 | Lowe | | 297/338 |
| 4,402,500 A * | 9/1983 | Coles | | 472/17 |
| 5,046,721 A * | 9/1991 | Altare | | 482/17 |
| 5,052,754 A * | 10/1991 | Chinomi | | 297/408 |
| 5,759,107 A * | 6/1998 | Nagel | | 472/47 |
| 5,792,031 A * | 8/1998 | Alton | | 482/78 |
| 6,264,278 B1 * | 7/2001 | Weimer et al. | | 297/423.26 |
| 6,800,062 B2 * | 10/2004 | Epley | | 600/558 |
| 7,691,073 B2 * | 4/2010 | Naganuma | | 601/98 |

\* cited by examiner

EXAMINATION CHAIR

BACKGROUND OF THE INVENTION

The present invention relates to an examination chair serving in particular to enable a practitioner to treat positional vertigo. The medical examination chair thus allows a seated person to be moved in a multidirectional mode and over large amplitudes, which is useful in dealing with such vertigo.

The inner ear of a human being enables the brain to identify the movements to which the person is subjected by means of three semicircular canals that are oriented in three substantially perpendicular planes. In addition, the vestibule receiver organ of the inner ear includes a zone that informs the brain on acceleration/deceleration phenomena, said zone being constituted in part by a gelatinous mass weighted by small crystals known as "otoliths" to the person skilled in the art. Positional vertigo can then be caused by the following phenomena that lead to erroneous perception of movements:

cupololithiasis caused by otoliths becoming detached and then migrating to the cupola cochlea which is a very sensitive portion of a semicircular canal; or canalolithiasis caused by otoliths that become detached and that move about in a semicircular canal.

While making a diagnosis, the practitioner moves the trunk and the head of the patient slowly through 180° in three planes: from front to back, laterally from one side to the other, and then in rotation about the axis of the body.

If positional vertigo is diagnosed, the practitioner moves the trunk and the head of the patient in a given plane rapidly followed by sudden deceleration. Thus, the otoliths that give rise to vertigo are expelled from the sensitive zone and the vertigo is generally cured in one to three sessions.

An examination chair is known that presents mobility about a vertical axis enabling a sitting patient to be turned. It is also possible to tilt the back of the chair so as to put the patient into a prone position, and it is also possible to lift the chair relative to its stand, usually by means of an electrically-controlled rack system, or possibly by a foot-controlled hydraulic system. This kind of chair mobility is largely sufficient for most examinations. However, the manipulations associated with diagnosing and treating positional vertigo cannot all be performed, since movement is possible in a single plane only and the manipulations are also wearisome both for the patient and for the practitioner.

Document FR 1 113 809 discloses apparatus for rehabilitation and checking reflexes, which apparatus includes an oscillating support, preferably having a plurality of degrees of freedom in movement, on which the patient is placed in such a manner as to be capable of damping or amplifying the oscillations of the support by moving the patient's own center of gravity.

That document is remote from the technical field of treating vertigo. The object of the device described is to stimulate the reflexes of a handicapped person, and not to move otoliths in the inner ear that lead to positional vertigo. In addition, it does not make it possible in any way to impart rapid movement followed by sudden deceleration.

The manipulations associated with diagnosing and treating vertigo therefore cannot be implemented in satisfactory manner with a device of known type.

Such manipulations are thus generally performed on an examination couch and they require a large amount of physical strength and know-how on the part of the practitioner, and also excellent co-operation on the part of patients. Unfortunately, this cannot be achieved with patients suffering from arthrosis, obesity, handicaps, or high levels of anxiety, which patients are consequently particularly difficult to treat, and that can lead to therapy failing.

In addition, the need to have available in a medical office both an examination couch and an examination chair considerably increases the amount of space that is needed and also the costs inherent in fitting out an office.

OBJECTS AND SUMMARY OF THE INVENTION

An object of the present invention is to provide a medical examination chair that enables a patient to be moved in three perpendicular planes, rapidly and over large amplitudes, up to 180° or more, while also making it possible to achieve sudden deceleration at the end of the movement.

According to the invention, a medical examination chair for seating and moving a patient in three substantially perpendicular planes over a large amplitude, comprises a primary arc connected to a stationary column via a horizontal shaft that constitutes a first axis of rotation, there being a second axis of rotation substantially perpendicular to the first axis of rotation that passes through first and second ends of said primary arc. In addition, the medical examination chair, includes a secondary arc that is provided with a seat and that is arranged inside the primary arc, being secured via third and fourth ends to the first and second ends respectively via an upper shaft and a bottom shaft, lying on the second axis of rotation, the primary and secondary arcs then being suitable for performing rotary movement about the first and second axes of rotation respectively. The invention is particularly remarkable in that it includes brake means for stopping the rotary movement suddenly.

Advantageously, the primary arc is connected to the horizontal shaft via the middle of its convex portion.

The practitioner can thus move a patient placed on the seat in rotation about the axis of the patient's own body, laterally from one side towards the other, and from front to back. In addition, the brake means enable the sudden deceleration to be generated that serves to expel any troublesome otoliths.

Furthermore, since the patient in the medical examination chair is set into movement as a whole, any problems that might be associated with lack of patient mobility or co-operation are eliminated. Patient comfort is thus increased and the manipulations performed are optimized and thus more effective.

In order to minimize the amount of force that needs to be delivered by the practitioner in order to set the primary arc and/or the secondary arc into movement, it is essential for centering to be correct, i.e. for the center of gravity of the patient to be as close as possible to the intersection of the first and second axes of rotation. For this purpose, the vertical position of the horizontal shaft on the stationary column is adjustable by using a rack and slider system, for example. Identically, the secondary arc can be moved relative to the first axis of rotation, using conventional means acting on the bottom and/or upper shaft in order to participate in adjusting centering.

Likewise, the position of the seat along the second axis of rotation is adjustable using a first actuator that is hydraulic or electrical, for example.

Advantageously, the examination seat of the invention has first and second motors respectively for turning the primary arc about the first axis of rotation and the secondary arc about the second axis of rotation. As a result, the practitioner no longer needs to exert force in order to move the patient, thus naturally making the practitioner's work easier.

In a first embodiment that is fully motorized, the brake means comprise the first and second motors. Since these first and second motors have large stepdown gear ratios, they can be stopped suddenly and thus perform the function required of the brake means.

In a second embodiment, the brake means comprise a first brake for suddenly stopping the primary arc, which brake may be hydraulic or electrical, e.g. braking on being unpowered. Similarly, the brake means are provided with a second brake for suddenly stopping the secondary arc, which second brake may be hydraulic or electrical.

In a third embodiment, the brake means comprises at least a first mechanical abutment for suddenly stopping the primary arc.

This first mechanical abutment, placed on a lateral side of the stationary column, is provided with a ring and a damper. At the end of the movement of the primary arc, a tooth of catch means thereof co-operates with the ring so as to block the primary arc, the damper then acting as a stop point.

Similarly, the brake means comprises a second mechanical abutment for suddenly stopping said secondary arc.

This second mechanical abutment is provided with at least one hook and at least one damper arranged on the first end of the primary arc. At the end of the movement of the secondary arc, the hook co-operates with stop means placed on the third end of the secondary arc in order to block the secondary arc, the damper then acting as a stop point.

The secondary arc can then turn about the second axis of rotation through almost 360°. Nevertheless, since certain manipulations consist in causing the patient to revolve several times, the stop means are advantageously retractable.

Furthermore, for patient comfort, the secondary arc is provided with at least one foot-rest that is secured to the seat. The position along the second axis of rotation of the assembly comprising the seat and the foot-rest is thus adjustable using the first actuator. In addition, the angle of inclination of the foot-rest relative to the second axis of rotation is also adjustable.

Similarly, the secondary arc possesses a seat back that is adjustable in height along the second axis of rotation and that is either secured to the foot-rest and seat assembly, or else is adjustable individually, e.g. by a second actuator.

Similarly, the medical examination chair preferably includes a headrest that can be tilted and adjusted in translation along the first and second axes of rotation using a third actuator, a control knob, and an indexing finger, for example.

In addition, since the patient needs to be set into movement, the medical examination chair is provided with at least one restraining means suitable for holding the patient to the medical examination chair via the head, the trunk, the pelvis, and the lower limbs, in particular the feet.

By way of example, these restraining means comprise adjustable armrests, shoulders, a head-band, straps, handles, and a harness.

In a computerized variant, the medical examination chair is provided with at least two position sensors and at least two movement sensors, each type of sensor being arranged on the primary arc and the secondary arc, for example, the sensors being connected to a control and management member controlling the medical examination chair, which member is provided with a display screen.

The position sensors serve to verify whether centering has been performed properly. The movement sensors serve to measure angular speed and acceleration, and also the total angular displacement achieved.

Manipulation can then be fully assisted by the control and management member which, when the medical examination chair is motor-driven, controls the first and second motors in particular on the basis of information provided by the sensors. In addition, if the medical examination chair is provided with first and second brakes, these brakes can be controlled by the control and management member.

A practitioner can thus use the present invention to move a patient and stop the imparted movement suddenly for the purpose of treating positional vertigo. In order to limit the amount of space occupied in the practitioner's office, the medical examination chair of the invention must also be capable of performing the functions of other existing items of equipment.

Thus, it includes first and second locking means respectively for preventing the primary arc from moving relative to the stationary column and for preventing the secondary arc from moving relative to the primary arc in a plurality of positions.

In addition, the medical examination chair includes a videonystagmoscope system which examines the eyes of the patient under infrared light in order to display on a screen the reflex displacements of the eyes that are known as "nystagmus" to the person skilled in the art, as occur during the various movements of the body. Optionally, this camera system may be connected, with or without wires, e.g. using high frequency transmission, to the control and management member, which is then provided with a device for analyzing nystagmus.

BRIEF DESCRIPTION OF THE DRAWINGS

The invention and its advantages appear in greater detail from the following description which relates to a preferred embodiment given without limiting character and described with reference to the accompanying figures, in which.

MORE DETAILED DESCRIPTION

Elements that are present in a plurality of distinct figures are given the same references in each of them.

Figure 1:
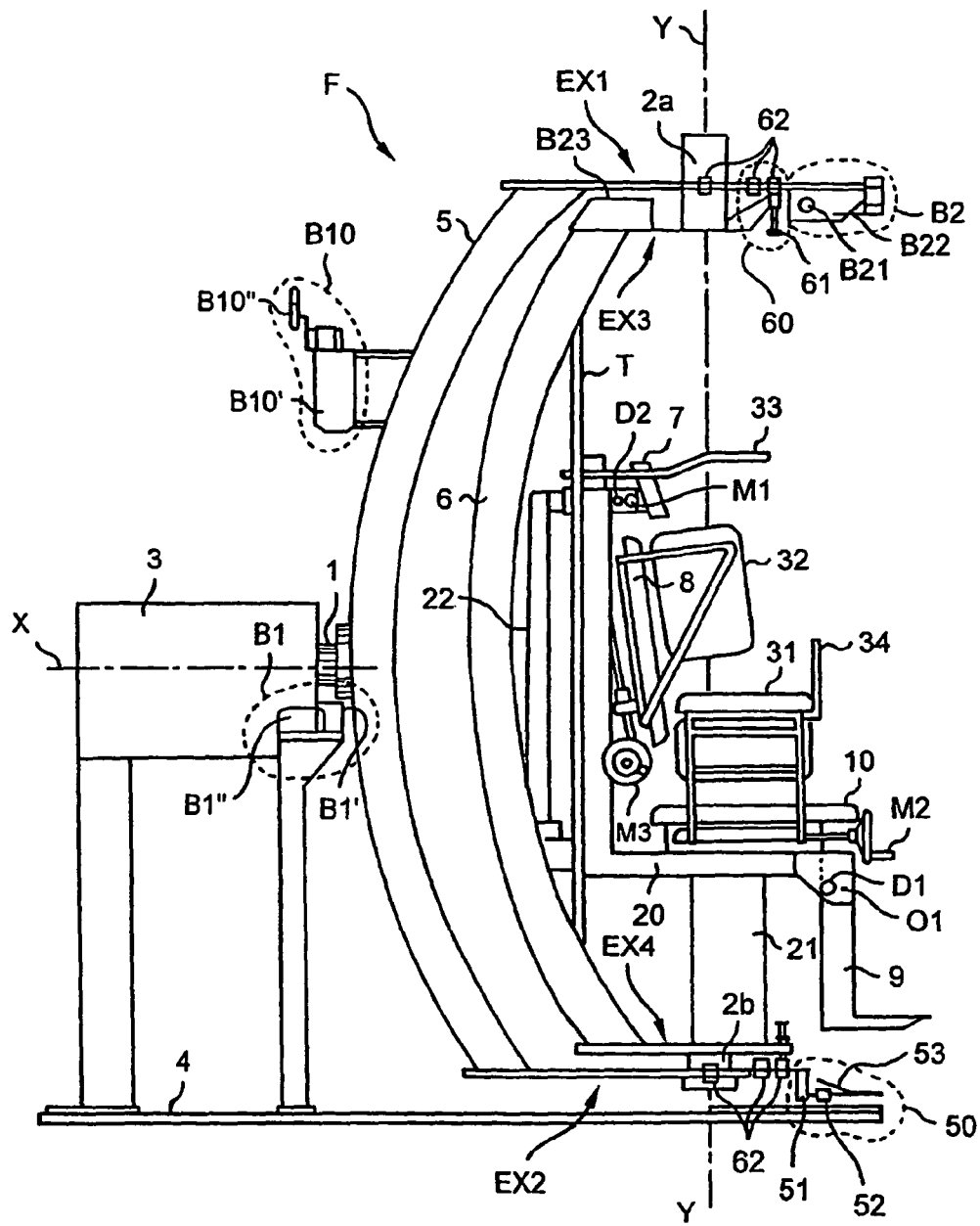
FIG. 1 is a side view of an examination chair of the invention.

FIG. 1 is a side view of a medical examination chair F of the invention.

The medical examination chair F as a whole is secured to a stationary column 3 via a horizontal shaft 1. This stationary column 3 is arranged on a stand 4 that rests on the floor and that is heavily weighted in order to prevent any toppling of the medical examination chair F regardless of the movements performed and the weight of the patient.

Naturally, any other system for securing the stationary column could be envisaged, e.g. a wall mount.

The primary arc 5 is secured to the horizontal shaft 1 via the middle of its convex portion and is capable of performing rotary movement about the first axis of rotation X.

The vertical position of the primary arc 5 is optionally adjustable in order to achieve optimized centering. The stationary column 3 may possibly be telescopic. Similarly, the primary arc 5 and/or the stationary column 3 may include a rack and slider system or any other equivalent adjustment system.

The secondary arc 6 is slightly smaller than the primary arc 5 and is received within it, being secured to upper and bottom shafts 2a and 2b disposed on the second axis of rotation Y intersecting the first and second ends EX1 and EX2 of the primary arc. Thus, the upper and bottom shafts 2a and 2b serve respectively to connect the first end EX1 to the third end EX3 of the secondary arc, and the second end EX2 to the fourth end EX4 of the secondary arc.

As a result, the secondary arc 6 is capable of performing rotary movement about the second axis of rotation Y.

The medical examination chair F comprises a frame 20 arranged on two rods T secured to the secondary arc 6 and carrying at least one foot-rest 9 and a seat 10. A first actuator 21 resting on the fourth end EX4 enables the position of the seat 10 and of the foot-rest 9 to be adjusted along the second axis of rotation Y.

Similarly, the secondary arc 6 includes a seat back 8. The position of the seat back may optionally be adjustable in translation along the second axis of rotation Y, sliding along the rod T, under drive from the first actuator when the seat back 8 is secured to the frame 20 or using an electrical second actuator when the back is independent of the frame 20.

In addition, the angle of inclination of the foot-rest 9 relative to the second axis of rotation Y is adjustable. Consequently, the foot-rest possesses a plurality of orifices O1 with a finger D1 being engaged in one of the orifices O1 in order to block the foot-rest 9 in a precise position.

The medical examination chair F is also provided with a headrest 7 whose angle of inclination and position along the first and second axes of rotation X and Y are adjustable. For this purpose, a third actuator 22 secured to the frame 20 contributes to adjusting the position of the headrest 7 along the second axis of rotation Y. Similarly, an indexing finger D2 adjusts the position of the headrest 7 along the first axis of rotation X, and a wheel M1 adjusts the angle of inclination of the headrest, via conventional means.

Consequently, the foot-rest 9, the seat 10, the seat back 8, and the headrest 7 all present a degree of adjustment that is sufficient for matching them to the size and the anatomy of each patient.

In addition, since the patient is to be set into motion, the patient needs to be secured to the medical examination chair F by restraining means comprising in particular armrests 31, shoulders 32, a padded head-band 33, retractable handles 34, a harness, and straps for holding the lower limbs, not shown in FIG. 1.

The armrests 31 and the shoulders 32 can be adapted to the anatomy of the patient since they are free to move laterally under drive from conventional means operated using first and second handles M2 and M3 respectively.

Similarly, the position of the head-band 33 along the first axis of rotation X is adjustable using conventional means.

Furthermore, in order to ensure that the medical examination chair F can be used as a conventional chair, it is essential to be able to prevent any rotary movement of the primary arc 5 and/or of the secondary arc 6.

Thus, the medical examination chair is provided with first and second locking means 50 and 60 respectively for the primary arc 5 and the secondary arc 6.

By way of example, the first locking means 50 is provided with a plate 51 having an orifice arranged under the second end EX2 of the primary arc 5. A finger 52 set into movement by a handle 53 then locks the primary arc 5 by being inserted in the orifice of the plate 51.

The second locking means 60 is constituted, for example, by a finger 61 secured to the third end EX3 of the secondary arc 6 and that is manually inserted in an orifice 62 in the first end EX1 of the primary arc. Advantageously, the first end EX1 has a plurality of orifices 62 so as to allow the secondary arc 6 to be locked in a plurality of positions. In addition, the second locking means 60 is duplicated, also being installed at the second and fourth ends EX2 and EX4.

The practitioner can cause the primary and secondary arcs 5 and 6 to turn respectively about the first and second axes of rotation X and Y manually by using handles for example, or by using first and second motors (not shown). In order to stop the medical examination chair F suddenly at the end of a rotary movement, the medical examination chair F includes brake means.

In a first embodiment (not shown in FIG. 1), the brake means comprise first and second motors with large stepdown gear ratios that enable them to be stopped instantaneously.

In a second embodiment (not shown in FIG. 1), the brake means comprise hydraulic or electrical brakes that enable the horizontal, upper, and/or bottom shafts 1, 2a, and/or 2b to be stopped suddenly, thus enabling any rotary movement of the primary and/or secondary arc 5 and/or 6 to be stopped.

With reference to FIG. 1, in a third embodiment, the brake means comprise first and second mechanical abutments B1 and B2 respectively for preventing the primary and secondary arcs 5 and 6 from moving at the end of a rotary movement.

The first mechanical abutment B1 is arranged on at least one lateral side of the column 3, and preferably on both lateral sides thereof. It is provided with a damper B1' and with a ring B1". Catch means B10 arranged on the primary arc 5 and provided with a toothed plate B10" and with a stop plate B10' co-operate with the first abutment B1 to stop the primary arc suddenly at the end of a rapid rotary movement thereof. As a result, the stop plate B10' is blocked suddenly by the damper B1', the ring B1" then being trapped by a tooth of the toothed plate B10". Rapid movement of the primary arc 5 then stops suddenly, thereby generating strong deceleration.

From the arrangement shown in FIG. 1 of the first mechanical abutments, the primary arc can perform rotary movement about the first axis of rotation X through an amplitude of 180°, and more precisely an amplitude of −90° to +90° relative to the vertical. Nevertheless, by arranging the mechanical abutments B1 differently, it is possible to envisage other amplitudes.

The second mechanical abutment B2 is arranged at the first end EX1 of the primary arc 5. It comprises at least one damper B21 and at least one hook B22. At the end of rapid rotary movement of the secondary arc 6 about the second axis of rotation Y, stop means comprising a plate B23 arranged on the third end EX3 co-operates with the second abutment B2. The plate B23 is thus stopped by the damper B22 and remains blocked in this position by being trapped by the hook B22.

Figure 2:
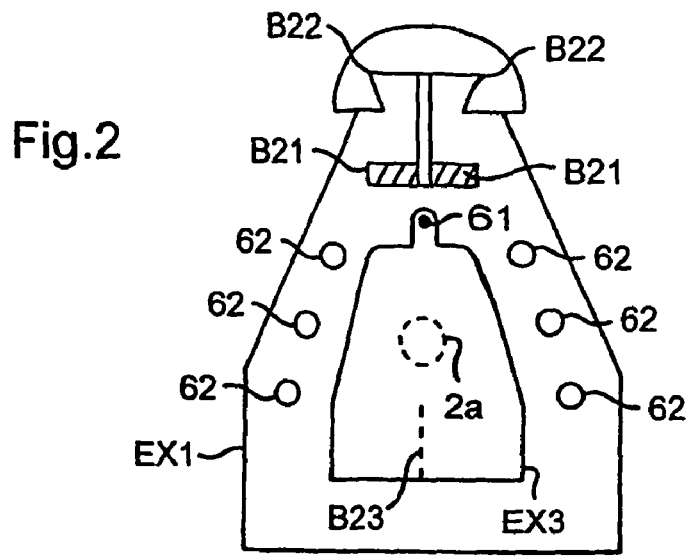
FIG. 2 is a view from beneath showing the second mechanical abutment.

FIG. 2 is a view from beneath of the first and third ends, showing in particular the second mechanical abutment. Since the secondary arc 6 can turn clockwise and counterclockwise, the second mechanical abutment has two dampers B21 and two hooks B22.

FIG. 2 also shows the finger 61 and the orifices 62 enabling the secondary arc 6 to be locked in position.

Figure 3:
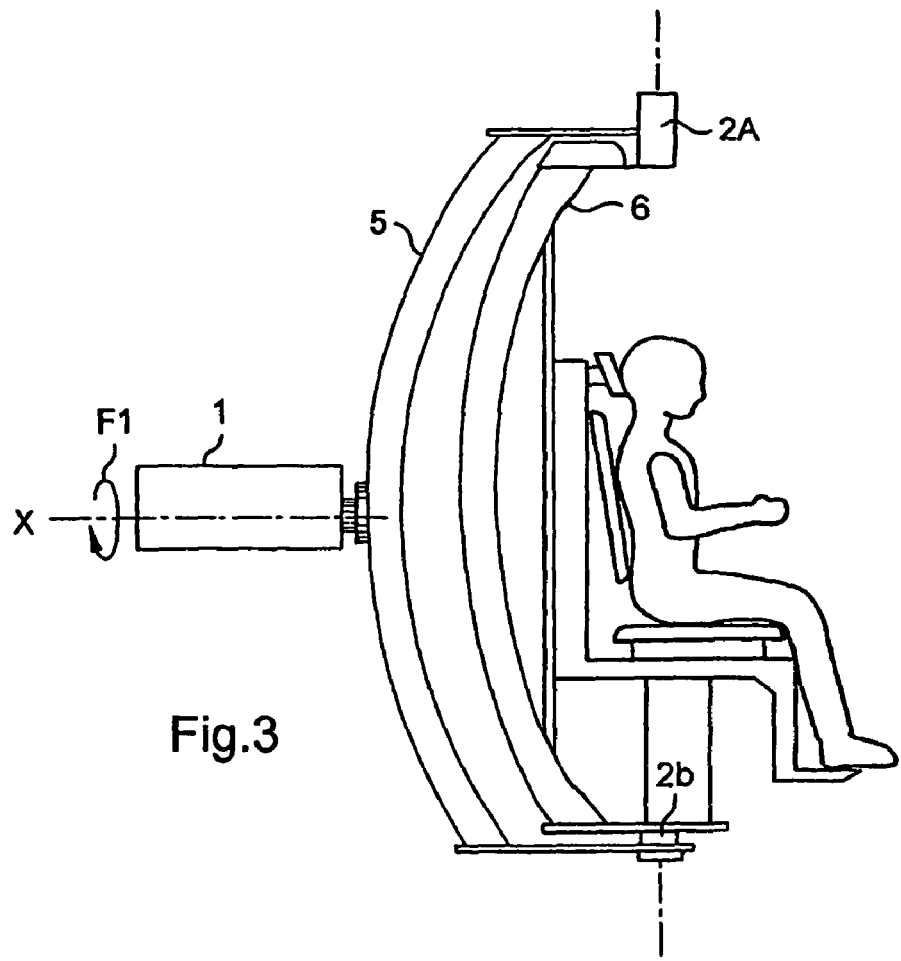
FIGS. 3, 4, and 5 are diagrams for explaining the modes of operation of the examination chair.
Figure 4:
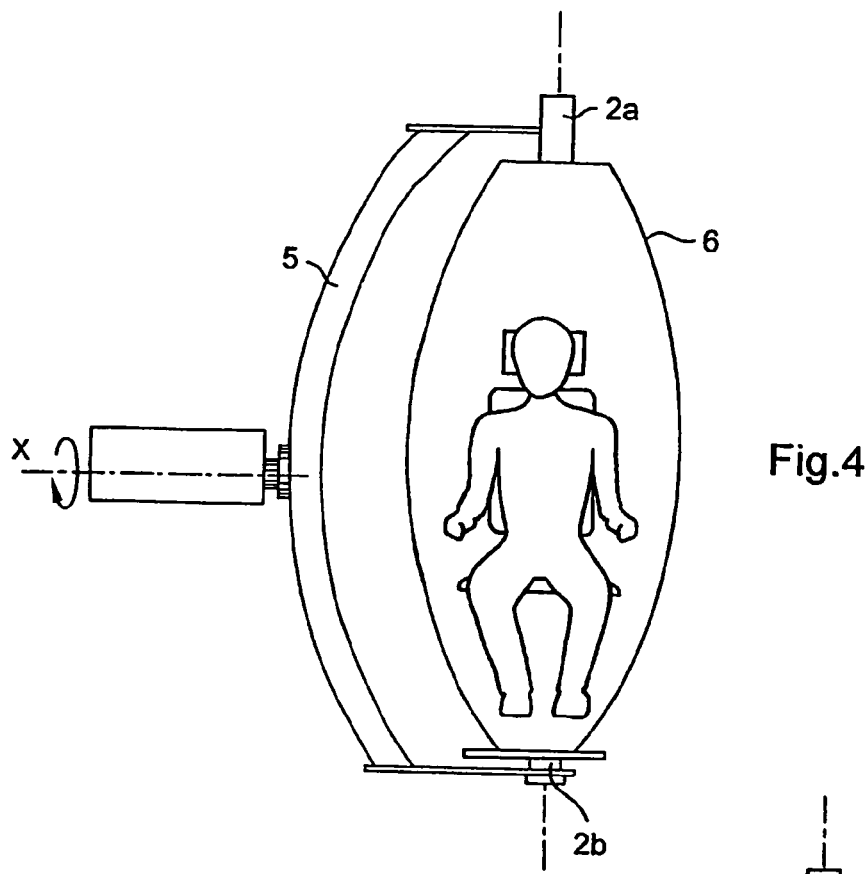
Figure 5:
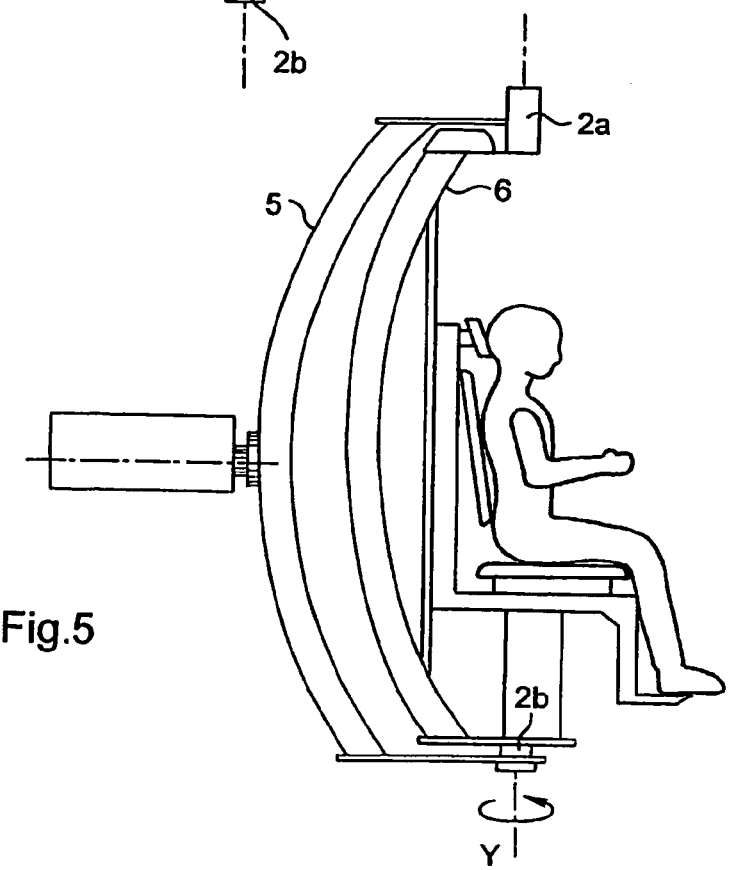

FIGS. 3, 4, and 5 show how a patient can be moved in three perpendicular planes.

With reference to FIG. 3, the secondary arc 6 is held stationary so that the back of the patient P is directed towards the horizontal shaft 1. By turning the primary arc about the axis X, the patient is moved laterally as a whole from one side to the other. Arrow F1 applies to a patient being moved from the patient's left towards the patient's right.

With reference to FIG. 4, the secondary arc 6 is turned through 90° and is then locked in this position. By turning the primary arc about the axis X, the patient is moved as a whole from front to back.

With reference to FIG. 5, the primary arc 5 is locked in the vertical position. By causing the secondary arc to turn about the axis Y, the patient is moved as a whole about the axis of the patient's trunk and head.

By performing the above-described movements and stopping them suddenly with the help of the instant braking means, a practitioner can treat positional vertigo.

With patients presenting certain types of vertigo, the examination chair F is thus particularly well adapted to performing specific diagnosis and therapy manipulations, enabling a patient to be moved as a whole in three perpendicular planes, thus relieving the practitioner of delivering physical force and also increasing the comfort of the patient concerned. The medical examination chair is mainly for use by a doctor specialized in otorhinolaryngology or in physiotherapy, but it can also be used by any qualified practitioner seeking to deal with this type of vertigo pathology.

Naturally, the present invention can be implemented in a wide variety of manners. It will be understood that it is not conceivable to identify exhaustively all possible implementations. Any of the means described may naturally be replaced by equivalent means without going beyond the ambit of the present invention.

What is claimed is:

1. A medical examination chair for seating and moving a patient, the medical examination chair comprising:
    a stationary column;
    a horizontal shaft supported by the stationary column, the horizontal shaft having a first axis of rotation;
    a primary arcuate member connected to the horizontal shaft and having a first end and a second end, the primary arcuate member having a toothed plate and a stop plate, wherein the primary arcuate member is configured for performing a first rotary movement about the first axis of rotation;
    a secondary arcuate member supported for rotation by the primary arcuate member about a second axis of rotation through the first end and the second end of the primary arcuate member, the secondary arcuate member arranged inside the primary arcuate member, the second axis of rotation substantially perpendicular to the first axis of rotation, wherein the secondary arcuate member is configured for performing a second rotary movement about the second axis of rotation;
    a seat supported by the secondary arcuate member;
    a first mechanical abutment supported by the stationary column to abruptly stop the primary arcuate member relative to the stationary column at an end of the first rotary movement of the primary arcuate member, the first mechanical abutment having a damper and a ring; and
    a second mechanical abutment supported by the primary arcuate member to abruptly stop the secondary arcuate member relative to the primary arcuate member at an end of the second rotary movement of the secondary arcuate member;
    wherein the damper is configured to block the stop plate, and the tooth of the toothed plate is configured to trap the ring, thereby suddenly stopping the first rotary movement of the primary arcuate member.

2. The medical examination chair of claim 1 wherein the first mechanical abutment is configured to limit the first rotary movement to an amplitude of 180 degrees.

3. The medical examination chair of claim 1 wherein the second mechanical abutment has a damper and a hook;
    wherein the secondary arcuate member has a plate; and
    wherein the damper is configured to block the plate and the hook is configured to trap the plate thereby suddenly stopping the second rotary movement of the secondary arcuate member.

4. A medical examination chair for seating and moving a patient, the medical examination chair comprising:
    a stationary column;
    a horizontal shaft supported by the stationary column, the horizontal shaft having a first axis of rotation;
    a primary arcuate member connected to the horizontal shaft and having a first end and a second end, wherein the primary arcuate member is configured for performing a first rotary movement about the first axis of rotation;
    a secondary arcuate member supported for rotation by the primary arcuate member about a second axis of rotation through the first end and the second end of the primary arcuate member, the secondary arcuate member having a plate, the secondary arcuate member arranged inside the primary arcuate member, the second axis of rotation substantially perpendicular to the first axis of rotation, wherein the secondary arcuate member is configured for performing a second rotary movement about the second axis of rotation;
    a seat supported by the secondary arcuate member;
    a first mechanical abutment supported by the floor stand to abruptly stop the primary arcuate member relative to the stationary column at an end of the first rotary movement of the primary arcuate member; and
    a second mechanical abutment supported by the primary arcuate member to abruptly stop the secondary arcuate member relative to the primary arcuate member at an end of the second rotary movement of the secondary arcuate member, the second mechanical abutment having a damper and a hook;
    wherein the damper is configured to block the plate, and the hook is configured to trap the plate, thereby suddenly stopping the second rotary movement of the secondary arcuate member.

* * * * *